(12) United States Patent
Podolski

(10) Patent No.: US 6,696,072 B1
(45) Date of Patent: *Feb. 24, 2004

(54) METHODS FOR TREATMENT OF MALE ERECTILE DYSFUNCTION

(75) Inventor: Joseph S. Podolski, The Woodlands, TX (US)

(73) Assignee: Zonagen, Inc., The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/494,627

(22) Filed: Jan. 31, 2000

Related U.S. Application Data

(62) Division of application No. 09/154,677, filed on Sep. 17, 1998, now Pat. No. 6,482,426.

(51) Int. Cl.⁷ .................................. A61K 9/08

(52) U.S. Cl. .................. 424/422; 514/559; 514/560

(58) Field of Search ................ 514/330, 929, 514/559–61; 424/422–23

(56) References Cited

U.S. PATENT DOCUMENTS

| | | | |
|---|---|---|---|
| 3,943,246 A | 3/1976 | Sturmer | 424/177 |
| 4,127,118 A | 11/1978 | Latorre | 128/79 |
| 4,139,617 A | 2/1979 | Grunwell et al. | 424/238 |
| 4,530,920 A | 7/1985 | Nestor et al. | 514/15 |
| 4,746,651 A * | 5/1988 | Goodman | |
| 4,801,587 A | 1/1989 | Voss et al. | 514/248 |
| 4,863,911 A | 9/1989 | Anderson, Jr. et al. | 514/176 |
| 4,885,173 A | 12/1989 | Stanley et al. | 424/440 |
| 5,059,603 A | 10/1991 | Rubin | 514/264 |
| 5,065,744 A | 11/1991 | Zusmanovsky | 128/79 |
| 5,079,018 A | 1/1992 | Ecanow | 426/385 |
| 5,145,852 A | 9/1992 | Virag | 514/253 |
| 5,236,904 A | 8/1993 | Gerstenberg et al. | 514/12 |
| 5,256,652 A | 10/1993 | El-Rashidy | 514/58 |
| 5,270,323 A | 12/1993 | Milne, Jr. et al. | 514/309 |
| 5,298,261 A | 3/1994 | Pebley et al. | 424/488 |
| 5,399,581 A | 3/1995 | Laragh et al. | 514/396 |
| 5,565,466 A | 10/1996 | Gioco et al. | 514/280 |
| 5,731,339 A | 3/1998 | Lowrey | 514/400 |

FOREIGN PATENT DOCUMENTS

| | | |
|---|---|---|
| EP | 0 357 581 | 3/1990 |
| WO | WO 95/05172 | 2/1995 |

OTHER PUBLICATIONS

AC–Di–Sol®, Croscarmellose Sodium, NF and Ph.Eur. The Premier Super Disintegrant for Wet and Dry Granulation Tablets And Capsules (Accelerates DisSolution) (Product Description Brochure); FMC Corporation, Philadelphia, Pa., pp. 1–9 (1988).

Althof, S.E. et al., "Sexual, Psychological, and Marital Impact of Self–Injection of Papaverine and Phentolamine: A Long–Term Prospective Study," *Journal Sex and Marital Therapy*, 17(2):101–112 (1991).

Azadzoi, K.M. et al., "Effects of Intracavernosal Trazadone Hydrochloride: Animal and Human Studies," *J. Urology*, 144(5):1277–1282 (Nov., 1990).

Barnett, A.J. et al., "The Action Of 'Regitine' In Man With Special Reference To Its Adrenergic Blocking Action," *Australasian Anals of Medicine*, 1:109–119 (1952).

Beavo, J.A. et al., In: *Advances in Second Messenger and Phosphoprotein Research*, Greengard et al., (eds.), vol. 22, pp. 1–38 (1988).

*Biotechnology Newswatch*, "Nice Try, but no Viagra, say experts reviewing new potency pills," pp. 4–5 (Jun., 1998).

Brindley, G.S., "Pilot experiments on the actions of drugs injected into the human corpus cavernosum penis," *Br. J. Pharmac.*, 87:495–500 (1986).

Brindley, G.S., "Cavernosal Alpha–Blockade: A new Technique for Investigating and Treating Erectile Impotence," *Brit. J. Psychiat.*, 143:332–337 (1983).

Brindley, G.S., "Cavernosal alpha–blockade and human penile erection," *J. Physiol.*, 342:24P (1983).

Corriere, J.N. Jr. et al., "Development of Fibrotic Penile Lesions Secondary to the Intracorporeal Injection of Vasoactive Agents," *J. Urology*, 140:615–617 (Sep., 1988).

Dawson, A. et al., "The Transient Anti–Hypertensive Effect of Phentolamine in Patients Receiving Beta–Blocker Treatment," *J. Int. Med. Res.*, 5:462–464 (1977).

Diedrichs, W. et al., "Reduction of Sympathetic Influence on Penile Erection by Phentolamine," *Urol. Int.*, 46:64–66 (1991).

Georgopoulos, A.J. et al., "Treatment of Chronic Heart Failure with Slow Release Phentolamine," *Europ. J. Clin. Pharmacol.*, 13:325–329 (1978).

Gissinger, D. et al., "A Comparative Evaluation of the Properties of some Tablet Disintegrant," *Drug Development and Industrial Pharmacy*, 6(5):511–536 (1980).

Godbillion et al., "Determination of the Major Metabolite of Phentolamine in Human Plasma and Urine By High–Performance Liquid Chromatography," *J. Chromatography*, 222:461–466 (1981).

Gould, L.A. et al., "Oral Therapy with Phetolamine in Chronic Congestive Heart Failure," *Chest*, 75(4):487–491 (Apr., 1979).

(List continued on next page.)

Primary Examiner—Edward J. Webman
(74) Attorney, Agent, or Firm—Howrey Simon Arnold & White, LLP

(57) ABSTRACT

Improved drug compositions and methods useful in the treatment of male erectile dysfunction. An optimized mixture of the drugs phentolamine mesylate, papaverine hydrochloride, and alprostadil in a buffer containing L-arginine and glycine is to be injected into the penile tissue to produce an erection in otherwise impotent men.

18 Claims, No Drawings

OTHER PUBLICATIONS

Gwinup, G., "Oral Phentolamine in Nonspecific Erectile Insufficiency," *Annals Internal Medicine*, pp. 162–163 (Jul., 1988).

Imhof, P.R. et al., "Human Pharmacology of Orally Administered Phentolamine," In: Phentolamine in Heart Failure and Other Cardiac Disorders, Taylor, S.H., and Gould, L.A., (eds.), Ben Huber, pp. 11–22 (1976).

Larsen, E.H. et al., "Fibrosis of Corpus Cavernosum After Intracavernous Injection of Phentolamine/Papaverine," *Journal Urology*, 137:292–293 (Feb., 1987).

Marriot, H.J.L., "An Alarming Pressor Reaction to Regitine," 46(5):1001–1002 (May, 1957).

McDonnell, S.M. et al., "Imipramine–induced Erection, Masturbation, and Ejaculation in Male Horses," *Pharmacol. Biochem. Behav. (USA)*, 27(1):187–191 (May, 1987) (*ABSTRACT*).

Montorsi, F. et al., "Clinical Reliability of Multi–Drug Intracavernous Vasoactive Pharmacotherapy for Diabetic Impotence," *Acta Diabetol.*, 31:1–5 (1994).

NIH Consensus Conference, "Impotence," NIH Concensus Development Panel on Impotence, *Journal American Medical Association*, 270(1):83–90 (1993).

Pfister et al., "Estimation of the Plasma Concentration and Course of Action of Phentol–amine Based On Its Inhibitory Effect On Adrenaline–Induced Platelet Aggregation," *Br. J. Clin. Pharmac.*, 5:175–180 (1978).

*Physicians' Desk Reference*, 37 Edition, pp. 409 and 864 (1983).

Ruskin, J.N. et al., "Primary Pulmonary Hypertension Treated With Oral Phentolamine," *Annals of Internal Medicine*, 90:772–774 (1979).

Schreiber, R. et al., "Hemodynamic Improvement following a Single Dose of Oral Phentolamine: Administration in Patients with Chronic Low Output Cardiac Failure," *Chest*, 76(5):571–575 (Nov., 1979).

Selvaag, O. et al., "Experiences with Regitin (A New Vasodilator Compound)," *Acta Medica Scandinavica, vol. CXLVI, fase. III*, pp. 209–215 (1953).

Sioufi, A. et al., "Gas Chromatographic Determination of Phenentolamine (Regitine) in Human Plasma and Urine," *Journal of Chromatography*, 222:429–435 (1981).

Sonda, L.P. et al., "The Role of Yohimbine for the Treatment of Erectile Impotence," *J. Sex & Marital Ther.*, 16(1):15–21 (1990).

Terrett, N.K. et al., "Sildenafil (VIAGRA™), A Potent and Selective Inhibitor of Type 5 cGMP Phosphodiesterase with Utility for the Treatment of Male Erectile Dysfunction," *Bioorganic & Medicinal Chemistry Letters*, 6(15):1819–1824 (1996).

*The Extra Pharmocopoeia: The authoritative reference work on drugs and medicines in current use*, Twenty–sixth Edition, 2 pages (1988).

Trapold, J.H. et al., "Pharmacological and Toxicological Studies on 2–(N–p'tolyl–N–(m'–Hydroxypheyl)–Aminomethyl)–Imidazoline (C–7337), a New Adrenergic Blocking Agent" pp. 119–127 (1950).

*United States Pharmacopeia*, Twentieth Revision, Official from Jul. 1, 1980, The National Formulary, Fifteenth Edition, Official from Jul. 1, 1980, U.S. Pharmacopeial Convention, Inc., Rockville, Md., pp. 615–617 (1979).

Virag, R. et al., "Intracavernous Injection of Papaverine as a Diagnostic and Therapeutic Method in Erectile Failure," *Angiology*, 35:79–87 (1984).

Virag, R., "Intracavernous Injection of Papaverine for Erectile Failure," *Lancet*, ii:938 (Oct., 1982).

Wagner, G. et al., "Buccal Phentolamine–A pilot trial for male erectile dysfunction at three separate clinics," *Int. J. Impotence Res.*, 6(Suppl. 1):D78 (1994).

Williams, Textbook of Endocrinology, p. 313 (Circa, 1976).

Zorgniotti, A.W., ""On Demand"Oral Drug For Erection In Impotent Men,"*J. Urology (AUA Eighty–Seventh Annual Meeting May 10–14, 1992)*, 147(4)(Suppl.):308A (Apr., 1992) (*ABSTRACT 382*).

Zorgniotti, A.W., "Experience with Buccal Phentolamine Mesylate for Impotence," *International Journal of Impotence Research*, 6(1):37–41 (Mar., 1994).

Zorgniotti, A.W. et al., "Auto–injection of the Corpus Cavernosum with a Vasoactive Drug Combination for Vasculogenic Impotence," *Journal Urology*, 133:39–41 (1985).

\* cited by examiner

METHODS FOR TREATMENT OF MALE ERECTILE DYSFUNCTION

CROSS REFERENCE TO RELATED APPLICATIONS

This application is a divisional of U.S. application Ser. No. 09/154,677 filed Sep. 17, 1998 now U.S. Pat. No. 6,482,426.

BACKGROUND OF THE INVENTION

This invention relates to improved drug compositions useful in the treatment of male erectile dysfunction and also to methods of treatment. More particularly, this invention discloses specific formulations containing the pharmacological agents phentolamine mesylate, papaverine hydrochloride, and alprostadil (prostaglandin E1) in a novel buffer and the administration of such formulations to mammals (including humans) to treat male impotence.

Impotence is a common medical disorder affecting about 20 million men in the U.S. alone. Male erectile dysfunction has been defined as the inability to achieve or maintain an erection sufficient for intercourse (Impotence, National Institutes of Health Consensus Development Panel on Impotence Conference, JAMA 1993, 270, 83–90). The dominant etiology for this condition is arterial insufficiency associated with cardiovascular disease. Male erectile dysfunction adversely impacts the quality of life, being frequently associated With depression, anxiety, and low self-esteem. Although male erectile dysfunction represents a major clinical problem, treatment for this condition remains problematic and unsatisfactory.

One of the least invasive therapies available entails the use of a vacuum constriction device on the penis to produce an erection. The physiology of the penis is such that blood flows in through arteries deep within the tissue while blood flows out through veins near the skin surface. By placing a plastic cylinder over the shaft of the penis and employing a vacuum pump to restrict venous blood flow from the penis, the corpus cavernosum penile tissue becomes engorged with trapped blood and an erection is produced. Common patient complaints are that this device is interruptive to the sex act, has a short duration of effectiveness, and can cause tissue damage to the penis, such as necrosis, with extended use.

Penile prosthesis implantation is an alternative treatment of erectile dysfunction. This therapy entails surgically implanting a mechanical device inside the penis (for example see U.S. Pat. No. 5,065,744 to Zumanowshky). This device can be a semi-rigid malleable rod or a fluid inflated tube which can be operated by the patient to achieve an erection. Although this method does not affect the ability to urinate, ejaculate, or have an orgasm, the surgery required to implant the prosthesis can lead to pain, infection, and scarring.

Recent insights into the physiological mechanism of penile erection have led to the development of other therapies for the treatment of erectile dysfunction. Preliminary studies have shown that during sexual arousal, nitric oxide molecules are released into the surrounding tissue from nerve endings and endothelial cells in the genitals. These nitric oxide molecules then cause the enzyme guanylate cyclase to produce cyclic guanosine monophosphate (cGMP) which lowers the level of intracellular calcium in the surrounding medium and allows for the relaxation of smooth muscle cells. In the penis, the relaxation of the corpus cavernosal smooth muscle cells permits increased blood flow into the cavernosal spaces which leads to greater intracavernosal pressure thereby producing penile rigidity.

It follows then that a pharmacological agent which inhibits the breakdown of cGMP would have the potential to prolong or enhance penile erections during sexual stimulation. The drug sildenafil (Viagra™, Pfizer, Inc.) is one such pharmacological agent which, when given orally, has shown some success in this manner (Terreft, N. K. et al. Bioorg. Med. Chem. Lett. 1996, 6, 1819–1824).

Other types of oral therapies which are available to treat erectile dysfunction by different means include centrally-acting drugs such as atipamezole (Farmos Orion) which is an α-adrenergic blocker, apomorphine (Pentech Pharmaceuticals) which is a dopaminergic agonist, and phentolamine (Vasomax™, Zonagen) which is another α-adrenergic blocker/vasodilator. This family of drugs appears to act by expanding arteries and relaxing penile tissue which, in combination, entraps blood in the penis thereby producing an erection. However, some oral therapies may have drawbacks with respect to efficacy and side effects. Therefore, in those cases it would be beneficial to treat impotence directly by administering medicaments directly on/into the penis itself. These modes of administration may also minimize the dosage of the medicament needed.

One alternative route for administering vasoactive agents like those mentioned above is by transdermal administration to the penis. The compound alprostadil (prostaglandin E1) is formulated as a cream (Macrochem) which is absorbed into the penile tissue. Alprostadil has been shown to bind to specific receptors in penile tissue which is accompanied by an increase in cellular cyclic adenosine monophosphate (cAMP) levels. The physiological mechanism, as described with cGMP above, results in a decrease of intracellular calcium in the cytoplasm and the relaxation of smooth muscle cells. These vasodilatory effects result in rapid arterial inflow and expansion of the sinusoidal spaces within the penis. This action then restricts venous outflow from the penis whereby penile rigidity develops. Another vasoactive agent, papaverine hydrochloride, is formulated into a patch (PharmaPatch, Pharmedia) to be applied to the skin of the penis and acts as a non-specific phosphodiesterase inhibitor to maintain cGMP levels in a similar sort of mechanism as described above which produces an erection. These external treatments of the skin surface of the penis suffer from the drawback that the sex partner comes into contact with the drug during intercourse and can be adversely affected.

The above-mentioned pharmacological agents and routes of administration represent therapies for the treatment of erectile dysfunction which can be successful for about 75–80% of the 20 million men having erectile dysfunction. However, for the remaining impotent population, a different treatment is needed which often includes intraurethral and/or. intracavernosal injection therapy.

Currently, there are two FDA-approved injection therapies available (Caverject®, Pharmacia-Upjohn; and Edex™, Schwartz Pharma), both of which employ alprostadil as the active component. Caverject® is commercially marketed as a freeze-dried powder containing the active ingredient alprostadil in a base of lactose, sodium citrate, and benzyl alcohol. When reconstituted with water, Caverject® is injected into the intracavernosal space of the penis. Similarly, EDEX™ is a lyophilized powder containing alprostadil, α-cyclodextrin, and anhydrous lactose. It is also reconstituted with water before injection into the intracavernosal space of the penis. A urethral suppository of alprostadil (MUSE™, Vivus, Inc.) has also recently been introduced into the market; however, it has shown disappointing clinical results (Biotech. Newswatch, Jun. 15, 1998, 4–5). Not all impotent men respond to alprostadil therapy alone.

In order to treat these individuals who were nonresponsive to alprostadil, Zorgniotti et al. (J. Urol. 133:39–41 (1985), incorporated herein by reference) demonstrated that the intracavernosal injection of a combination of papaverine hydrochloride and phentolamine mesylate rapidly produced transitory penile tumescence which could be followed by an erection in response to sexual stimulation.

Similarly, Althof et al. (J. Sex Marital Ther. 17(2): 101–112 (1991), incorporated herein by reference) reported that intracavernosal injection of papaverine hydrochloride and phentolamine mesylate resulted in improved erectile ability in about 84% of patients injected. However, there was a high dropout rate (57%) in this study because 25% of patients developed fibrotic nodules, 30% had abnormal liver functions, and 19% experienced bruising of the penile tissue. In another study using the same combination of phentolamine mesylate and papaverine hydrochloride, the intracavernous injection of this combination led to marked penile fibrosis in the patients injected (see Larsen, E. K. et al. J. Urol. 137, 292–293 (1987) incorporated herein by reference).

Therefore, a need exists for a safe and effective alternative treatment for impotence which minimizes the drawbacks of the currently available therapies described above.

SUMMARY OF THE INVENTION

Compositions and methods for the treatment of male erectile dysfunction are provided. When injected into the corpus cavernosum, the compositions of this invention aid in producing, enhancing, or sustaining an erection of the penis. The compositions comprise one or more of the following pharmaceutically active agents: an α-adrenergic blocker, a phosphodiesterase inhibitor, and a prostaglandin. Preferred α-adrenergic blockers include phentolamine mesylate and phentolamine hydrochloride. Preferred phosphodiesterase inhibitors include papaverine hydrochloride, Sildenafil (Pfizer). Preferred prostaglandins include alprostadil, any pharmaceutically acceptable salts, hydrates, hemihydrates, ester or other pharmaceutically acceptable forms of the foregoing pharmaceutically active agents are also included within the scope of the invention. Other Class V phosphodiesterase inhibitors are also preferred. A preferred composition is a trimix comprising phentolamine mesylate, alprostadil and papaverine hydrochloride. Preferably, the trimix further comprises a buffer which buffer comprises a substrate for nitric oxide synthetase. A preferred substrate is arginine.

Preferred buffers include one or more substrates for nitric oxide synthetase. More preferred buffers comprise glycine, arginine, or mixtures thereof. Even more preferably, the buffer comprises a mixture of glycine, L-arginine, mannitol, and benzyl alcohol in water. The foregoing buffers may also comprise other pharmaceutical excipient carriers and the like. The advantages to the use of these buffer in conjunction with the mentioned active agents include improved solubility profiles of the pharmaceutical agents and they provide substrates for the enzyme nitric oxide synthetase, which has been shown to play a role in the erectile response, and may result in a lower dosage requirement for efficacy.

DETAILED DESCRIPTION OF THE INVENTION

The present invention is directed to improved compositions which, by way of a non-limiting example, comprise the vasoactive agents phentolamine mesylate, papaverine hydrochloride, and alprostadil (or any pharmaceutically acceptable salts of these vasoactive agents). Another aspect of the invention is directed to compositions comprising one or more vasoactive agents such as papaverine, phentolamine, and alprostadil in a buffer comprising either glycine, L-arginine, or a mixture of glycine and L-arginine. By virtue of the improved solubility profiles of the vasoactive agents in the buffers of the present invention, the use of the inventive compositions lowers the incidence of fibrotic nodules in the penis and priaprism caused by precipitation and depot formation of vasoactive agents at the site of injection. Without being bound by theory, it is also believed that the presence of L-arginine in the compositions of the invention or other substrates for nitric oxide synthetase may lower the effective dosage of the vasoactive agents in the compositions.

When compositions according to the present invention comprise only an α-adrenergic blocker or a phosphodiesterase inhibitor or a prostaglandin as the pharmaceutically active agent, the composition will further comprise a buffer which buffer comprises a substrate for nitric oxide synthetase such as arginine. When the compositions of the invention comprise two or more of the pharmaceutically active agents described above, the compositions optionally comprise buffers which comprise a substrate for nitric oxide synthetase.

Particularly preferred for the present purposes is a composition comprising an α-adrenergic blocker (e.g., phentolamine mesylate), a phosphodiesterase inhibitor (e.g., papaverine hydrochloride or Sildenifil), and a prostaglandin (e.g., alprostadil) in a buffer. The active ingredients phentolamine mesylate, papaverine hydrochloride, and alprostadil are present in the composition in a weight ratio in the range of about 0.5:7.5:0.005 to about 5:30:0.02. More preferably, the weight ratio of phentolamine mesylate: papaverine hydrochloride: alprostadil is about 1:30:0.01.

Dosages of the vasoactive components of the invention are in the range of about 0–40 μg/ml alprostadil, about 0–50 mg/ml papaverine, and about 0–10 mg/ml phentolamine in a total volume of about 0.5 ml. Preferred dosages of the inventive compositions are in the range of about 1.25–5 mg/ml phentolamine, about 7.5–30 mg/ml papaverine, and about 5–20 μg/ml alprostadil in a total volume of about 0.5 ml. More preferably, the dose is about 1 mg/ml phentolamine, about 30 mg/ml papaverine, and about 0.01 mg/ml alprostadil in a total volume of about 0.5 ml.

In the case of a composition of the invention containing only phentolamine as the vasoactive agent in combination with a buffer such as an arginine and/or glycine containing buffer, the preferred dosage is about 1.25 mg/ml in a total volume of 0.5 ml. For a composition containing only papaverine in combination with an arginine and/or glycine contains buffer as the vasoactive agent, the preferred dosage is about 7.5 mg/ml in a total volume of 0.5 ml. In a composition containing only alprostadil as the vasoactive agent in an arginine and/or glycine containing buffer, the preferred dosage is about 5 μg/mi in a total volume of 0.5 ml. Compositions comprising only two of the vasoactive agents in a buffer according to the present invention are also contemplated by the invention.

The active ingredients are administered in a buffer which enhances their solubility and/or provides a substrate for nitric oxide synthetase. The buffer preferably contains glycine, mannitol, and benzyl alcohol in water. In this buffer, the content of glycine is preferably in the range of about 1% to about 2% by weight. More preferably, the buffer contains L-arginine, glycine, and other pharmaceutically acceptable excipients such as mannitol, and benzyl alcohol in water. The weight ratio of L-arginine to glycine in this preferred buffer is about 1:20. The pH of the composition in buffer is from about 3 to about 7. A preferred pH range for the composition is from about 3 to about 5.

Also included in the present inventions is a method for the treatment of male erectile dysfunction which comprises administering a pharmacologically effective amount of a composition comprising an α-adrenergic blocker, a phosphodiesterase inhibitor, and a prostaglandin. Preferably, in this method the composition comprises phentolamine mesylate, papaverine hydrochloride, and alprostadil in a buffer. In this method of treatment, the route of administration is a member of the group consisting of oral, transdermal, subcutaneous intraperitoneal, intramuscular, and intrapenile (including intracavernosal). A preferred route of administration is by intracavernosal injection.

The composition utilized in this method of treatment preferably comprises phentolamine mesylate, papaverine hydrochloride, and alprostadil in a weight ratio in the range of about 0.5:7.5:0.005 to about 5:30:0.02. More preferably, phentolamine mesylate, papaverine hydrochloride, and alprostadil are present in the composition in a weight ratio of about 1:30:0.01.

Dosages of the vasoactive agents useful in this method of treatment are in the range of about 0–40 μg/ml alprostadil, about 0–50 mg/ml papaverine, and about 0–10 mg/mi phentolamine in a total volume of about 0.5 ml. Preferred dosages of the vasoactive agents are in the range of about 1.25–5 mg/ml phentolamine, about 7.5–30 mg/ml papaverine, and about 5–20 μg/ml alprostadil in a total volume of about 0.5 ml. More preferably, the dose in this method is about 1 mg/ml phentolamine, about 30 mg/ml papaverine, and about 0.01 mg/ml alprostadil in a total volume of about 0.5 ml.

Methods utilizing a composition containing only phentolamine as the vasoactive agent, the preferred dosage rate is about 1.25 mg/ml in a total volume of 0.5 ml. For a method utilizing a composition containing only papaverine as the vasoactive agent, the preferred dosage rate is about 7.5 mg/ml in a total volume of 0.5 ml. In a method using a composition containing only alprostadil as the vasoactive agent, the preferred dosage rate is about 5 pg/ml in a total volume of 0.5 ml.

The buffer used to solubilize the active ingredients in the foregoing methods comprises mixtures of glycine, mannitol, and benzyl alcohol in water. The glycine content of this buffer is preferably in the range of about 1% to about 2% by weight. More preferably, the buffer comprises a mixture of glycine, L-arginine, mannitol, and benzyl alcohol in water. The weight ratio of glycine to L-arginine in the preferred buffer is about 1:20. The pH of the composition of the invention in the buffer is from about 3 to about 7. Preferred is a pH from about 3 to about 5.

The present invention is further illustrated by the following examples which assess the increased solubility of the active ingredients phentolamine, papaverine, and alprostadil in a buffer comprising glycine and arginine and also the ability of the improved compositions to induce penile erection in rabbits upon the intracavemosal injection of the composition containing phentolamine mesylate, papaverine hydrochloride, and alprostadil in buffer at various pH. The use of the composition of the present invention for treatment of impotence in humans is also provided.

The foregoing specification and Examples are intended to illustrate the present invention and are not intended to limit the scope of the invention as set out in the appended claims.

EXAMPLE 1

Solubility of Phentolamine-Papaverine in Glycine-Arginine Buffer at Various pH

Papaverine is sparingly soluble (<1 mg/ml) in the presence of phentolamine at physiological pH. Under these conditions papaverine may precipitate producing a deposit of solid drug at the injection site. This deposit of solid papaverine could act as a depot of drug which continues to exert its effects on erectile ability over time increasing the risk for priaprism and the occurrence of nodules/fibrosis in the penis.

In order to address this problem, the buffers at the injection site comprising glycine, arginine, or a mixture of glycine and L-arginine were prepared in an attempt to promote the solubility of the active ingredients papaverine and phentolamine and to provide substrate for nitric oxide synthetase. A series of saturated solutions containing the pharmaceutically active ingredients in buffer at various pH were prepared, filtered, then analyzed by a high performance liquid chromatograph (HPLC) with an ultraviolet wavelength detector to determine the concentration of the dissolved phentolamine and papaverine active ingredients.

Saturated solutions of papaverine hydrochloride and solid phentolamine mesylate at a constant ratio of about 6 to about 1 were added in the amounts indicated in Table 1 to buffer containing about 0.1 M glycine and about 2 mM L-arginine, initial pH 8.2. A 0.1 N solution of NaOH was used to adjust the pH to the indicated values. These solutions were shaken for about 10 minutes then held at room temperature overnight in order to allow maximum dissolution of drugs in the buffer. The samples were then filtered through a 0.45 μ PFTE filter to remove undissolved drug and analyzed by high pressure liquid chromatography (HPLC) to determine how much of each drug went into solution at the various pH values. HPLC was performed using a C18 column having a mobile phase of buffer (5 mM $NaH_2PO_4$ and 5 mM octane sulfonic acid, pH 3) in 30% acetonitrile with a flow rate of 1.5 ml/minute. The detection wavelength was 210 nm. Standard curves of both phentolamine and papaverine were prepared in order to determine the concentration of the phentolamine-papaverine mixtures in the samples by measurement of peak area.

TABLE 1

Solubility of Papaverine Hydrochloride and Phentolamine Mesylate in a Mixture vs. pH in buffer of 0.1M glycine and 2 mM Arginine

| | Papaverine (mg/ml) | | Phentolamine (mg/ml) | |
|---|---|---|---|---|
| pH | Added to Buffer | In Solution | Added to Buffer | In Solution |
| 3.91 | 66 | 36.81 | 11 | 12.12 |
| 4.35 | 60 | 7.75 | 10 | 9.88 |
| 5.04 | 60 | 0.7 | 10 | 6.5 |
| 7.48 | 60 | 0.17 | 10 | 4.97 |
| 7.65 | 60 | 0.2 | 10 | 6.99 |

The data demonstrates that for papaverine the solubility was about 36.81 g/ml in the glycine-arginine buffer at pH 3.91. In contrast, in a glycine-arginine buffer of pH 7.48 the solubility was only about 0.2 mg/ml . Therefore, the use of a buffer containing glycine and L-arginine at a pH of about 3–5 enhances the solubility of papaverine in contrast to a buffer having a pH greater than 7.0. Similarly, the solubility of phentolamine in the mixture was, in general, greater at lower pH. However, at pH 7.65 an increase in solubility of phentolamine was seen. The increased solubility of the vasoactive drugs in the buffers of the present invention reduces the possibility that the drugs will form depots at the site of invention.

EXAMPLE 2

Intracavernosal Injection of Trimix Formulations

Four New Zealand white rabbits were utilized in this study to determine the effects of the intracavernosal injection of two formulations of the compositions of the present invention. The compositions comprised a trimix of alprostadil, phentolamine mesylate and papaverine hydrochloride. The detailed compositions are listed in Table 2 below. The content formulations of A and B are similar except that formulation B contains no L-arginine.

TABLE 2

Composition of Injectable Trimix Formulations

|  | Formulation A (per ml) | Formulation B (per ml) |
| --- | --- | --- |
| Alprostadil | 20 µg | 20 µg |
| Phentolamine Mesylate | 5 mg | 5 mg |
| Papaverine HCl | 30 mg | 30 mg |
| L-Arginine | 0.35 mg | None |
| Glycine | 7.5 mg | 7.5 mg |
| Mannitol | 24 mg | 24 mg |
| Benzyl alcohol | 8.4 mg | 8.4 mg |
|  | Final pH: 3.98 | Final pH: 4.01 |
|  | Sterile filtered | Sterile filtered |

Two of the rabbits underwent intracavernosal injections of solution A and the other two rabbits underwent intracavernosal injections of solution B. In preparation for these injections, the rabbits were anesthetized by intramuscular injection of ketamine (35 mg/kg) and xylazine (5 mg/kg). Anesthesia was maintained with 0.2 ml intravenous bolus injections of pentobarbital (25 mg/ml) as needed. A 20 gauge angiocatheter was placed into the carotid artery for on-line measurement of systemic arterial pressure. A 23 gauge mini-catheter was placed intracavernosally for measurement of intracavernosal pressure during erection. Baseline arterial blood pressure and intracavernosal pressure were recorded. Once baseline had been established, 0.2 ml of either solution A or solution B was injected intracavernosally. The effects of intracavernosal drug administration on intracavernosal pressure and systemic arterial pressure were continuously recorded. Further intracavernosal injections were made if full penile erection was not produced.

The results indicate that the first rabbit given an intracavernosal injection of 0.2 ml of solution A experienced a full penile erection lasting more than 30 minutes. The intracavernosal pressure, a measurement of engorgement, increased from about 30 mm Hg to about 63 mm Hg (91% of mean systemic arterial pressure after injection). The only side effect noted was a minor hypotension event lasting for approximately 10 seconds. There was no effect on heart rate.

The second rabbit given an intracavernosal injection of 0.2 ml of solution A also experienced a full penile erection lasting about 4 minutes. The intracavernosal pressure after injection rose from about 35 mm Hg to about 69 mm Hg (83% of mean systemic arterial pressure). This rabbit was injected intracavernosally a second time with 0.2 ml of solution A which produced another full penile erection lasting more than 30 minutes. After the second intracavernosal injection, the intracavernosal pressure increased from about 28 mm to about 65 mm Hg (96% of mean systemic arterial pressure). The only side effect noted was a minor transient hypotension which lasted for about 8 seconds. There was no effect on heart rate.

The third rabbit received an intracavernosal injection of 0.2 ml of solution B which produced a partial erection lasting for 3 minutes. The first injection increased intracavernosal pressure from about 36 mm Hg to about 50 mm Hg (60% of mean systemic arterial pressure). The second injection produced a full penile erection lasting for over 30 minutes. After the second intracavernosal injection, intracavernosal pressure increased from about 28 mm Hg to about 65 mm Hg (96% of mean systemic arterial pressure). The only side effect noted was a minor transient hypotension lasting for approximately 6 seconds. There was no effect on heart rate.

The fourth rabbit received two injections, each 0.2 ml of solution B, which failed to produce an erection and caused only a minor increase in intracavemosal pressure from about 15 mm Hg to about 33 mm Hg. A third injection of 0.2 ml of solution B produced a partial erection increasing intracavernosal pressure from about 30 mm Hg to about 45 mm Hg (64% of mean systemic arterial pressure). A fourth injection of 0.2 ml of solution B caused a full penile erection lasting for about 15 minutes. After the fourth injection the intracavernosal pressure increased from 42 mm Hg to about 65 mm Hg (88% of systemic arterial pressure). After every injection a transient minor hypotension lasting for 5–8 seconds was observed. There was no change in heart rate.

These experiments demonstrate that the intracavernosal administration of solution A or solution B produced penile erection in the rabbit. Erectile response to solution A occurred after one injection in the first rabbit and after two injections in the second animal. Erectile response to solution B occurred after two injections in the first animal and after four injections in the second animal. Therefore, it appears that both solutions A and B containing the active ingredients phentolamine mesylate, papaverine hydrochloride, and aiprostadil in buffers of either glycine or glycine-arginine provide effective treatment of male erectile dysfunction; however, the number of injections needed to produce an erection in the rabbit was less using solution A than solution B. Solution A containing L-arginine appears then to be more effective as an impotence therapy than solution B. The invention also contemplates the use of one or more of each of the foregoing vasoactive agents in buffers containing substrates for nitric acid synthetase. As described above, preferred buffers include glycine and arginine and pharmaceutically acceptable excipients and/or carriers.

EXAMPLE 3

Treatment of Impotence in Humans

Although the foregoing examples described the effect of a trimix of alprostadil, phentolamine mesylate, and papaverine hydrochloride in buffers with or without arginine on erectile function in rabbits, dosages for administration to humans of vasoactive agents in the compositions of the present invention may be readily determined by one of ordinary skill in the art. For example, appropriate base-line dosages may be determined by reference to Zorgniotti, et al. (J. Urol. 133:39–41, 1985) who demonstrated that intracavemosal injection of 30 mg of papaverine in combination with 0.5 to 1 mg phentolamine (total volume of one ml) produced penile erection in response to sexual stimulation.

Dosages of the vasoactive agents useful in the compositions and methods of the present invention are in the range of about 0.5 to about 40 pg/ml alprostadil, about 0.5 to about 50 mg/ml papaverine, and about 0.5 to about 10 mg/ml phentolamine in a total volume of about 0.5 ml. Preferred dosages of the inventive compositions are in the range of about 1.25–5 mg/ml phentolamine, about 7.5–30 mg/ml papaverine, and about 5–20 μg/ml alprostadil in a total volume of about 0.5 ml. More preferably, the dose in this method is about 1 mg/ml phentolamine, about 30 mg/ml papaverine, and about 0.01 mg/ml alprostadil in a total volume of about 0.5 ml. Erectile response may be measured by any of several criteria well known in the art.

According to the invention, the use of arginine or other substrates for nitric oxide synthesis in combination with vasoactive substances including phentolamine and/or alprostadil and/or papaverine may enhance or restore sexual response or responsiveness in impotent men when compared to the composition without arginine or other nitric acid synthetase substrates. The presence of arginine or other nitric oxide synthetase substrates may also allow the use of smaller dosages of the vasoactive agents resulting in a more cost-effective therapy, with fewer side effects.

The foregoing specification is intended to illustrate the present invention but is not intended to limit the invention as set out in the appended claims. Still other variations within the spirit and scope of the present invention are possible and will readily present themselves to those skilled in the art.

I claim:

1. A method for the treatment of male erectile dysfunction which comprises administering to a male in need thereof a pharmacologically effective amount of a composition comprising an α-adrenergic blocker, a phosphodiesterase inhibitor, and a prostaglandin in a buffer, wherein said buffer comprises a substrate for nitric oxide synthetase.

2. The method of claim 1 wherein the α-adrenergic blocker is pentholamine mesylate, or any pharmaceutically acceptable salt thereof.

3. The method of claim 1 wherein the phosphodiesterase inhibitor is papaverine hydrochloride or any pharmaceutically acceptable salt thereof.

4. The method of claim 1 wherein the prostaglandin is alprostadil.

5. The method of claim 1 wherein the buffer comprises L-arginine and, optionally, a pharmaceutically acceptable excipient or carrier.

6. The method of claim 5 wherein the buffer comprises glycine having a pH range of from about 3 to about 5.

7. The method of claim 1 wherein the buffer comprises a mixture of arginine and glycine having a pH range of from about 3 to about 5.

8. The method of claim 1 wherein the buffer comprises glycine and L-arginine in a weight ratio of about 1:20.

9. The method of claim 7 wherein the buffer further comprises benzyl alcohol and mannitol and has a pH range of from about 3 to about 5.

10. The method of claim 1 wherein the weight ratio of phentolamine mesylate: papaverine hydrochloride: alprostadil is about 0.5:7.5:0.005 to about 5:30:0.02.

11. The method of claim 1 wherein the weight ratio of phentolamine mesylate: papaverine hydrochloride: alprostadil is about 1:30:0.01.

12. The method of claim 1 wherein the dosage of phentolamine mesylate, papaverine hydrochloride, and alprostadil are in the range of about 0–40 μg/ml alprostadil, about 0–50 mg/ml papaverine, and about 0–10 mg/ml phentolamine.

13. The method of claim 1 wherein the dosage of phentolamine mesylate, papaverine hydrochloride, and alprostadil are in the range of about 1.25–5 mg/ml phentolamine, about 7.5–30 mg/ml papaverine, and about 5–20 μg/ml alprostadil.

14. The method of claim 1 wherein the dosage of phentolamine mesylate, papaverine hydrochloride, and alprostadil are about 1 mg/ml phentolamine, about 30 mg/ml papaverine, and about 0.01 mg/ml alprostadil.

15. The method of claim 12, 13, or 14 wherein the vasoactive agents are present in a total volume of 0.5 ml.

16. The method of claim 1 wherein the dosage of alprostadil is about 5 μg/ml in a total volume of 0.5 ml.

17. The method of claim 1 wherein the dosage of phentolamine is about 1.25 mg/ml in a total volume of 0.5 ml.

18. The method of claim 1 wherein the pH range of the buffer is from about 3 to about 7.

* * * * *